US009420799B2

(12) United States Patent
Pedersen et al.

(10) Patent No.: US 9,420,799 B2
(45) Date of Patent: Aug. 23, 2016

(54) METHOD FOR CONTROLLING NEMATODE PESTS

(75) Inventors: Palle Pedersen, Stanton, MN (US); Clifford George Watrin, Minnetonka, MN (US); Michael Oostendorp, Stein (CH); Andre Luiz Freitas de Oliveira, Greensboro, NC (US)

(73) Assignee: Syngenta Participations AG, Basel (CH)

( * ) Notice: Subject to any disclaimer, the term of this patent is extended or adjusted under 35 U.S.C. 154(b) by 361 days.

(21) Appl. No.: 14/000,478

(22) PCT Filed: Apr. 13, 2012

(86) PCT No.: PCT/EP2012/056796
§ 371 (c)(1),
(2), (4) Date: Aug. 20, 2013

(87) PCT Pub. No.: WO2012/140207
PCT Pub. Date: Oct. 18, 2012

(65) Prior Publication Data

US 2013/0340123 A1 Dec. 19, 2013

Related U.S. Application Data

(60) Provisional application No. 61/475,839, filed on Apr. 15, 2011.

(51) Int. Cl.

| | |
|---|---|
| ***A01N 43/36*** | (2006.01) |
| ***A01N 63/00*** | (2006.01) |
| ***A01N 51/00*** | (2006.01) |
| ***A01N 63/04*** | (2006.01) |

(52) U.S. Cl.
CPC ................ *A01N 63/00* (2013.01); *A01N 43/36* (2013.01); *A01N 51/00* (2013.01); *A01N 63/04* (2013.01)

(58) Field of Classification Search
None
See application file for complete search history.

(56) References Cited

U.S. PATENT DOCUMENTS 7,154,021 B2 * 12/2006 Hauge .................. C07K 14/415 800/265
9,149,044 B2 * 10/2015 Pedersen ................ A01N 63/02
2010/0034792 A1 * 2/2010 Becker ..................... A01C 1/08 424/93.46

FOREIGN PATENT DOCUMENTS

| | | |
|---|---|---|
| WO | 2009/124707 A2 | 10/2009 |
| WO | 2010/030554 A1 | 3/2010 |
| WO | 2010/108616 A1 | 9/2010 |
| WO | 2012/038476 A1 | 3/2012 |
| WO | 2012/038480 A2 | 3/2012 |

OTHER PUBLICATIONS

Mitchum et al. Plant Disease, 91:1473-1476 (2007).*
International Search Report for International Patent Application No. PCT/EP2012/056796.

* cited by examiner

*Primary Examiner* — Medina A Ibrahim
(74) *Attorney, Agent, or Firm* — Brian D. McAlhaney

(57) ABSTRACT

Plant propagation material expressing soybean cyst nematode resistance can be treated with a nematode-antagonistic biocontrol agent. Use of the nematode-antagonistic biocontrol agent can reduce the rate at which soybean cyst nematode (SCN) pests acquire tolerances to pesticidal activity of soybean plants expressing SCN resistance and pesticides, and can also increase yield and pesticidal activity.

20 Claims, No Drawings

METHOD FOR CONTROLLING NEMATODE PESTS

This application is a 371 of International Application No. PCT/IB2012/056796 filed Apr. 13, 2012 which claims priority to U.S. Provisional Patent Application No. 61/475,839 filed Apr. 15, 2011, to which the contents of all are incorporated herein by reference.

FIELD OF TECHNOLOGY

The present technology relates generally to the control of pests which cause damage to soybean plants by their feeding activities, and more particularly the control of soybean cyst nematode (SCN) pests by the combination of soybean seed having a soybean cyst nematode resistant trait and the treatment of the soybean seed with a nematicide prior to planting the seed.

BACKGROUND

Insects and related pests are commonly known to damage agricultural crops. The damage to the crops adversely affects the yield of such crops. One such pest known to damage crops is the nematode. There are many types of nematode pests, one such nematode is the soybean cyst nematode (SCN), *Heterodera glycines* Ichinohe. SCN causes substantial losses in soybean production. Yield suppression attributed to *H. glycines* resulted in an estimated $750 million in losses to U.S. soybean producers annually from 2003 to 2005 (Wrather, J. A., and Koenning, S. R. 2006. Estimates of disease effects on soybean yields in the United States 2003 to 2005. J. Nematol. 38:173-180).

Generally, seed treatments can protect the developing seedling from seed and soil borne pathogens and insect pests, as well as early foliar diseases and insects. Seed treatments can control pathogens and insects with very much reduced rates of active ingredient (a.i.) compared with soil or foliar applications. As the a.i. is restricted to the region around the seed and to those pathogens and insects attacking the developing seedling, seed treatments give biological, environmental and economical benefits.

Some varieties of soybean have been bred to express a characteristic in the plant which reduces damage due to the SCN. Soybean genetic resistance to SCN have been found in various resistant sources, for example, Plant Introduction (PI) lines PI88788, PI548402 and PI437654 are resistant cultivars available to soybean producers for use in breeding programs against SCN. PI88788, for example, is the source of resistance for a large percentage of soybeans grown in the soybean market. PI8878 is popular with growers because of its ability to deliver resistance in combination with high yield, among other reasons.

However, in light of the methods currently used to control nematode pests, applicants believe there remains a further need for increased control of nematode pests. Certain pest control methods are proposed in the literature. However, these methods are not fully satisfactory in the field of pest control, which is why there is a demand for providing further methods for controlling and combating pests and for protecting plants, especially crop plants. This object is achieved according to the present technology. There is also a need to reduce the rate at which pests acquire an increasing tolerance to both pest resistant crop plants and pesticides. For example, applicants desire to reduce the rate at which pests acquire resistance to lines having, inter alia, high yield, such as PI88788 for example. Applicants also desire to extend the useful life of both pest resistant crop plants and pesticides.

SUMMARY

By way of summary, the current disclosure is directed to, inter alia, a variety of methods, compositions, and propagation material. In one embodiment, the disclosure includes a method for preventing damage by a pest to a plant seed and/or the seed's resulting propagation by treating an SCN resistant soybean seed with at least one nematicide.

An embodiment includes a method for increasing pesticidal activity on nematode pests by treating plant propagation material expressing SCN resistance with nematicide.

An embodiment includes a method for reducing the rate at which pests acquire increased tolerances to soybeans expressing an SCN resistant gene trait (i.e., SCN resistant soybeans) and pesticides by implementing a dual-mode of action to control the pest. The first mode being the use of an SCN resistant soybean and the second being the use of pesticides applied to the plant seed. The present technology is also directed to extending the useful life of both SCN resistant soybeans and pesticides by implementing a dual-mode of action to control the pest.

An embodiment includes plant propagation material expressing SCN resistance which is treated with at least one nematicide, optionally treated with at least one insecticide. The treated plant propagation material provides for a reduction of pest damage to a plant seed and/or the seed's resulting propagation (e.g. plant shoots, stems and foliage).

An embodiment also includes a method of increasing yield in soybean plants expressing SCN resistance by treating the soybean seed with a nematicide in the substantial absence of pest pressure, and specifically in the substantial absence of SCN pest pressure. The nematicide preferably being a nematode-antagonistic biocontrol agent or a synthetic nematicide. It should also be clear, that in some aspects, the present disclosure is inclusive of methods of increasing yield in soybean plants expressing SCN resistance in the presence of SCN pest pressure.

The above summary was intended to summarize certain embodiments of the present disclosure. Systems, methods and compositions will be set forth in more detail, along with examples demonstrating efficacy, in the figures and detailed description below. It will be apparent, however, that the detailed description is not intended to limit the present invention, the scope of which should be properly determined by the appended claims.

DETAILED DESCRIPTION

In accordance with the present technology, the treatment of unsown, SCN resistant-soybean plant seeds treated with a composition that includes at least one nematicide has excellent pest control characteristics. Characteristics may include protecting the plant seed from pests as well as increased protection of the plant from SCN pest damage.

In many examples, the use of nematicides for controlling SCN on SCN resistant soybean plants, which contain for instance, genes expressing SCN resistance activity, shows a high control of SCN pests.

In particular, it has been found that within the scope of technology that treating plant seeds expressing SCN resistance with at least one nematicide having activity against SCN has advantageous properties, which include, inter alia, increased pesticidal activity and an extended useful pesticidal life of both the SCN resistant plant and the nematicide.

The extension of the useful pesticidal life both the SCN resistant plant and the pesticide is achieved through the dual-mode action of the pesticides. The dual-mode of action refers to the application of a pesticide to a plant, plant seed, or plant propagation material, which expresses SCN resistance. Generally, when a single mode of action is used (i.e., either the pesticide alone, or the SCN resistant plant alone), the pest, over time, may obtain an increased tolerance to a single mode of action. This increased tolerance may necessitate the use of increased pesticidal dosages, or may render the mode of action wholly ineffective at controlling pests. However, with a dual-mode or action, this increased tolerance is slowed which effectively extends the useful life of both the pesticide and the SCN resistant plant.

As mentioned above, the advantageous properties are not limited to pesticidal activity and the extension of useful pesticidal lives, but refer to numerous synergistic properties of the present technology compared with the nematicide and the SCN resistant plant alone. Examples of such additional advantageous properties may include at least one of: extension of the pesticidal spectrum of action to other pests, for example to resistant strains; reduction in the application rate of the nematicides, or sufficient control of the pests with the aid of the compositions according to the invention even at an application rate of the nematicides alone and the plant alone are ineffective; improved quality of produce such as higher content of nutrient or oil, enhanced shelf life, reduced content of toxic products such as mycotoxins, reduced content of residues or unfavorable constituents, better digestability; improved tolerance to unfavorable temperatures, drought tolerance, enhanced assimilation rates such as nutrient uptake, water uptake and photosynthesis; favorable crop properties such as altered leaf area, increased yields, favorable-germination properties, flower set increase, or other advantages known to those skilled in the art.

The nematicides suitable for use in the present technology comprise at least one member selected from the group consisting of a nematode-antagonistic biocontrol agent, such as nematophagous fungi and nematophagous bacteria, and synthetic nematicides.

The term "nematode-antagonistic biocontrol agent" as used herein refers to an organism that inhibits nematode activity, growth or reproduction, or reduces nematode disease in plants or an organism which produces substances, e.g. proteins, chemicals, etc. toxic to nematodes or substances that inhibit hatching.

"Inhibition of nematode growth" refers to any aspect by which nematode disease in a plant is reduced, including, but not limited to, slowing nematode growth; reducing reproduction, hatching, mate and host-finding; and killing nematodes.

The present technology also provides embodiments in which the nematode-antagonistic biocontrol agent includes a nematophagous fungi, such as, but not limited to, ARF18 (Arkansas Fungus 18); *Arthrobotrys* spp., for example, *Arthrobotrys oligospora, Arthrobotrys superb* and *Arthrobotrys dactyloides; Chaetomium* spp., for example, *Chaetomium globosum; Cylindrocarpon* spp., for example, *Cylindrocarpon heteronema; Dactylaria* spp., for example, *Dactylaria candida; Exophilia* spp., for example, *Exophilia jeanselmei* and *Exophilia pisciphila; Fusarium* spp., for example, *Fusarium aspergilus* and *Fusarium solani; Gliocladium* spp., for example, *Gliocladium catenulatum, Gliocladium roseum* and *Gliocladium vixens; Harposporium* spp., for example, *Harposporium anguillulae; Hirsutella* spp., for example, *Hirsutella rhossiliensis* and *Hirsutella minnesotensis; Lecanicillium* spp., for example, *Lecanicillium lecanii* (=*Verticillium lecanii*); *Meristacrum* spp., for example, *Meristacrum asterospermum; Monacrosporium* spp., for example, *Monacrosporium drechsleri, Monacrosporium gephyropagum* and *Monacrosporium cionopagum; Myrothecium* spp., for example, *Myrotehcium verrucaria; Nematoctonus* spp., for example, *Nematoctonus geogenius, Nematoctonus leiosporus; Neocosmospora* spp., for example, *Neocosmospora vasinfecta; Paecilomyces* spp., for example, *Paecilomyces lilacinus; Pochonia* spp., for example, *Pochonia chlamydosporia* (=*Vercillium chlamydosporiumi*); *Stagonospora* spp., for example, *Stagonospora heteroderae* and *Stagonospora phaseoli*; and vesicular-arbuscular mycorrhizal fungi.

The present technology also provides embodiments in which the nematode-antagonistic biocontrol agent includes a nematophagous bacteria, such as, but not limited to, obligate parasitic bacteria, opportunistic parasitic bacteria, rhizobacteria, parasporal Cry protein-forming bacteria, endophytic bacteria and symbiotic bacteria. In particular embodiments, the biocontrol agent can be a bacteria species selected from *Actinomycetes* spp., *Agrobacterium* spp., *Arthrobacter* spp., *Alcaligenes* spp., *Aureobacterium* spp., *Azobacter* spp., *Beijerinckia* spp., *Burkholderia* spp., *Chromobacterium* spp., *Clavibacter* spp., *Clostridium* spp., *Comomonas* spp., *Corynebacterium* spp., *Curtobacterium* spp., *Desulforibtio* spp., *Enterobacter* spp., *Flavobacterium* spp., *Gluconobacter* spp., *Hydrogenophage* spp., *Klebsiella* spp., *Methylobacterium* spp., *Phyllobacterium* spp., *Phingobacterium* spp., *Photorhabdus* spp., *Rhizobium* spp., *Serratia* spp., *Stenotrophomonas* spp., *Xenorhadbus* spp. *Variovorax* spp., *Pasteuria* spp., *Pseudomonas* spp., *Bacillus* spp., and *Paenibacillus* spp.

As a non-limiting example, the bacterial biological control agents can include endoparasitic bacterium of the genus *Burkholderia cepacia; Pasteuria*, e.g. *Pasteuria penetrans, Pasteuria thornei, Pasteuria nishizawae, Pasteuria ramosa*, Candidatus *Pasteuria usgae* sp. nov.; *Brevibacillus laterosporus* strain G4; *Pseudomonas fluorescens; Corynebacterium paurometabolu, Corynebacterium pauronietabolum; Paenibacillus macerans*; Rhizobacteria; bacterium of the genus *Bacillus*, e.g. *Bacillus* sp B 16, *Bacillus agri, Bacillus aizawai, Bacillus albolactis, Bacillus amyloliquefaciens, Bacillus cereus, Bacillus coagulans, Bacillus endoparasiticus, Bacillus endorhythmos, Bacillus firmus, Bacillus kurstaki, Bacillus Iacticola, Bacillus lactimorbus, Bacillus lactis, Bacillus laterosporus, Bacillus lactimorbus, Bacillus licheniformis, Bacillus megaterium, Bacillus medusa, Bacillus metiens, Bacillus natto, Bacillus nigrificans, Bacillus popillae, Bacillus pumilus, Bacillus siamensis, Bacillus sphaericus, Bacillus spp., Bacillus subtilis, Bacillus thuringiensis* (including those forming Cry proteins toxic to nematodes and/or nematode larvae such as Cry5, Cry6, Cry12, Cry13, Cry14 and Cry21), *Bacillus thuringiensis* israelensis; *Bacillus thuringiensis* kurstaki, *Bacillus uniflagellates*, plus those listed in the category of *Bacillus* Genus in the "Bergey's Manual of Systematic Bacteriology, First Ed. (1986)" alone or in combination. In a particularly preferred embodiment, the nematicidal biological control agent is at least one *B. firmus* CNCM 1-1582 spore and/or *B. cereus* strain CNCM 1-1562 spore as disclosed in U.S. Pat. No. 6,406,690, which is incorporated herein by reference in its entirety. In other preferred embodiments, the bacteria is at least one *B. amyloliquefaciens* IN937a, at least one *Bacillus subtilis* strain designation GB03, or at least one *B. pumilus* strain designation GB34. Combinations of the four species of above-listed bacteria, as well as other spore-forming, root-colonizing bacteria known to exhibit agriculturally beneficial properties are within the scope and spirit of the present invention. Particularly preferred embodiments according to the invention are also those compositions that comprise mutants of *B. firmus* CNCM 1-1582 spore and/or *B. cereus* strain CNCM 1-1562 spore. Very particularly preferred are those mutants that have a nematicidal activity.

Examples of synthetic nematicides include acibenzolar-S-methyl, an avermectin (e.g., abamectin), carbamate nematicides (e.g., aldicarb, thiadicarb, carbofuran, carbosulfan, oxamyl, aldoxycarb, ethoprop, methomyl, benomyl, alanycarb), organophosphorus nematicides (e.g., phenamiphos (fenamiphos), fensulfothion, terbufos, fosthiazate, dimethoate, phosphocarb, dichlofenthion, isamidofos, fosthietan, isazofos ethoprophos, cadusafos, terbufos, chlorpyrifos, dichlofenthion, heterophos, isamidofos, mecarphon, phorate, thionazin, triazophos, diamidafos, fosthietan, phosphamidon), and certain fungicides, such as captan, thiophanate-methyl and thiabendazole.

The term "avermectin" refer to any of the members of the avennectin class of compounds, which are disclosed as milbemycins and avenmectins, for example, in U.S. Pat. Nos. 4,310,519; and 4,427,663. Avenmectins are known to the person skilled in the art. They are a group of structurally closely related pesticidally active compounds that are obtained by fermentation of a strain of the microorganism *Streptomyces avermitilis*. Derivatives of avermectins can be obtained via conventional chemical syntheses. "Abamectin" is a mixture of avermectin $B_{1a}$ and avermectin $B_{1b}$ and is described, for example, in The Pesticide Manual, 10.sup.th Ed. (1994), The British Crop Protection Council, London, page 3. The designation "abamectin" and "avenmectin" include derivatives. Acceptable avermectins useful in the invention include, for example, ivermectin, doramectin, selamectin, emamectin, and abamectin.

Preferred nematicides include ARF18; *Arthrobotrys* spp.; *Chaetomium* spp.; *Cylindrocarpon* spp.; *Exophilia* spp.; *Fusarium* spp.; *Gliocladium* spp.; *Hirsutella* spp.; *Lecanicillium* spp.; *Monacrosporium* spp.; *Myrothecium* spp.; *Neocosmospora* spp.; *Paecilomyces* spp.; *Pochonia* spp.; *Stagonospora* spp.; vesicular-arbuscular mycorrhizal fungi, *Burkholderia* spp.; *Pasteuria* spp., *Brevibacillus* spp.; *Pseudomonas* spp.; Rhizobacteria; *Bacillus* spp.

Particularly preferred nematicides include ARF18, *Arthrobotrys oligospora, Arthrobotrys dactyloides, Chaetomium globosum, Cylindrocarpon heteronema, Exophilia jeanselmei, Exophilia pisciphila, Fusarium aspergilus, Fusarium solani, Gliocladium catenulatum, Gliocladium roseum, Gliocladium vixens, Hirsutella rhossiliensis, Hirsutella minnesotensis, Lecanicillium lecanii, Monacrosporium drechsleri, Monacrosporium gephyropagum, Myrotehcium verrucaria, Neocosmospora vasinfecta, Paecilomyces lilacinus, Pochonia chlamydosporia, Stagonospora heteroderae, Stagonospora phaseoli*, vesicular-arbuscular mycorrhizal fungi, *Burkholderia cepacia, Pasteuria penetrans, Pasteuria thornei, Pasteuria nishizawae, Pasteuria ramosa, Brevibacillus laterosporus* strain G4, *Pseudomonas fluorescens*, Rhizobacteria and *Bacillus thuringiensis.*

Some varieties of soybean have been bred to express a characteristic in the plant which reduces damage due to the SCN. Soybean genetic resistance to SCN have been found in various resistant sources, for example, Plant Introduction (PI) lines PI88788, PI548402, PI437654, PI90763, PI209332, PI89882 and PI548316. These indictor lines are suitable for use as the source of resistance in breeding programs against SCN. SCN resistant soybeans include these PI lines as well as any cultivars developed from these indicator lines. Resistance of soybean to soybean cyst nematode can be defined on the basis of nematode reproduction on a soybean genotype compared to a susceptible standard (cv. Lee) (Schmitt, D. P., and J. G Shannon. 1992. Differentiating soybean responses to *Heterodera glycines* races. Crop Science 32:275-277). This relationship of reproduction on a range of hosts is further used to classify susceptibility and resistance. These classifications do not utilize crop response in terms of yield. Levels of resistance categories (Schmitt and Shannon, 1992) are based on a modification of the original scheme for the classification of races of soybean cyst nematode (Golden, A. M., J. M. Epps, R. D. Riggs, L. A. Duclos, J. A. Fox, and R. L. Bernard. 1970. Terminology and identity of infraspecific forms of the soybean cyst nematode *Heterodera glycines*. Plant Disease Reporter 54:544-546). The Female Index, used to classify resistance, is defined as: FI=(number of eggs produced by the nematode on a test cultivar/number of eggs produced on Lee the susceptible check)*100.

The nematicidally-effective amount of a given nematicide will vary, depending upon factors including, but not limited to, the plant species, the surface area of the seed, the type of carrier, presence or absence of other active ingredients, the method of formulation, the route of delivery, the specific nematicide used including the different fungi or bacteria species, the target nematode species, and the seriousness of the nematode infection or damage to the plant(s).

"A nematicidally effective amount" as used herein refers to an amount of nematicide capable of killing, controlling, or infecting nematodes, retarding the growth or reproduction of nematodes, reducing a nematode population, and/or reducing damage to plants caused by nematodes.

The method according to the invention allows pests of the abovementioned type to be controlled, i.e. contained, repelled or destroyed, which occur, in particular, on SCN resistant plants.

Depending on the intended aims and the prevailing circumstances, the pesticides within the scope of the technology, which are known per se, are generally formulated as emulsifiable concentrates, suspension concentrates, directly sprayable or dilutable solutions, spreadable pastes, dilute emulsions, wettable powders, soluble powders, dispersible powders, dusts, granules or encapsulations in polymeric substances which comprise a nitroimino- or nitroguanidino-compound.

The active ingredients are employed in these compositions together with at least one of the auxiliaries conventionally used in art of formulation, such as extenders, for example solvents or solid carriers, or such as surface-active compounds (surfactants).

Formulation auxiliaries which are used are, for example, solid carriers, solvents, stabilizers, "slow release" auxiliaries, colourants and, if appropriate, surface-active substances (surfactants). Suitable carriers and auxiliaries are all those substances which are conventionally used for crop protection products. Suitable auxiliaries such as solvents, solid carriers, surface-active compounds, non-ionic surfactants, cationic surfactants, anionic surfactants and other auxiliaries in the compositions employed according to the invention are, for example, those which have been described in EP-A-736 252.

The action of the compositions within the scope of the technology which comprise nematicidal compounds can be extended substantially and adapted to prevailing circumstances by adding other insecticidally, acaricidally and/or fungicidally active ingredients. Suitable examples of added active ingredients include: neonicitinoid compounds such as thiamethoxam, imidacloprid, clothianidin, thiacloprid or acetamiprid; beta-cyfluthrin, cyantraniliprole, diafenthiuron, diazinon, emamectin, emamectin benzoate, fenoxycarb, fipronil, flonicamid, lambda-cyhalothrin, methiocarb, pymetrozine, pyriproxyfen, pyrifluquinazon, spinetoram, spinosad, spirotetramat, tefluthrin, thiodicarb or Ti-435. As an example, formulated compositions for applying to seeds generally comprise 0.1 to 99%, in particular 0.1 to 95%, of a nematicidal compound and 1 to 99.9%, in particular 5 to 99.9%, of at least one solid or liquid auxiliary, it being possible, for 0 to 25%, in particular 0.1 to 20%, of the compositions to be surfactants (% in each case meaning percent by weight). While concentrated compositions are more preferred as commercial products, the end user will, as a rule, use dilute compositions which have considerably lower concentrations of active ingredient.

Formulated compositions may also comprise other solid or liquid auxiliaries, such as stabilisers, for example epoxidized or unepoxidized vegetable oils (for example epoxidized coconut oil, rapeseed oil or soya bean oil), antifoams, for example silicone oil, preservatives, viscosity regulators, binders and/or tackifiers, and also fertilizers or other active ingredients for achieving specific effects, for example, bactericides, fungicides, nematicides, molluscicides or herbicides.

Compositions can be produced in a known manner, for example prior to mixing with the auxiliary/auxiliaries by grinding, screening and/or compressing the active ingredient, for example to give a particular particle size, and by intimately mixing and/or grinding the active ingredient with the auxiliary/auxiliaries.

The methods according to the invention for controlling pests of the abovementioned type is carried out in a manner known per se to those skilled in the art, depending on the intended aims and prevailing circumstances, that is to say by spraying, wetting, atomizing, dusting, brushing on, seed dressing, scattering or pouring of the composition. In the case of spore forming bacteria and fungi, the application rates with respect to plant propagation material (e.g. seed treatment) preferably range from about $1\times10^5$ to $1\times10^{12}$ (or more) spores/seeds. Preferably, the spore concentration is about $1\times10^6$ to about $1\times10^{11}$ spores/seed. For the synthetic nematicides, preferred rates include at least 0.03 mg active ingredient (a.i.)/seed, preferably from 0.03 to 0.5 mg a.i./seed.

The propagation material can be treated with the composition prior to application, for example, seed being dressed prior to sowing. The active ingredient may also be applied to seed kernels (coating), either by soaking the kernels in a liquid composition or by coating them with a solid composition.

Examples of formulations of nematicidal compounds which can be used in the method according to the invention, for instance solutions, granules, dusts, sprayable powders, emulsion concentrates, coated granules and suspension concentrates.

Yield Response Experiment

The yield response study illustrates the unexpected increase in yield achieved by using a nematode-antagonistic biocontrol agent with SCN resistant varieties, e.g. those exhibiting HG Type 2 resistance such resistance sourced from PI88788. Multiple field trials were conducted across the United States Midwest region. Baseline nematode populations were determined by sampling from 4 untreated plots. Samples were taken (10 cores per plot) at a depth of 6-8 inches (approx. 15.2-20.3 cm). Samples were stored in a cooler until laboratory assays (eggs/100 cc) were performed.

To allow for sufficient viability to assess results properly, both SCN resistant and susceptible varieties were treated with an insecticide and fungicide seed treatment (CRUISER-MAXX seed treatment for beans available from Syngenta Crop Protection, LLC including thiamethoxam (22.61%); mefenoxam (1.70%) and fludioxonil (1.12%)). In addition for some test groups *Pasteuria nishizawae* treatment was applied at a rate of approximately $1\times10^7$ spores/seed. Percent yield increase was determined by comparing seeds treated with *Pasteuria* to those not treated with *Pasteuria*.

The results of 119 separate trials were sorted according to initial SCN pressure at trial location. Yield data were averaged.

| SCN Pressure (eggs/100 cc) | Yield Response for Resistant Varieties | Yield Response for Susceptible Varieties |
|---|---|---|
| >1000 | 5.2% | 0.0% |
| 501-1000 | 2.6% | 0.8% |
| 1-500 | 0.7% | 1.0% |
| 0 | 0.3% | 1.3% |

As the data clearly show, resistant varieties treated with *Pasteuria* showed increase yield over non-*Pasteuria* treated soybean seed regardless of pest pressure. The greater the pest pressure, the more dramatic the increase in yield. Soybean varieties having no resistance or tolerance to SCN pests generally benefitted from treatment with *Pasteuria*, although this benefit was mostly seen in the absence of pest pressure or with low pest pressure.

According to the invention, the rate at which SCN pests acquire tolerances to soybean plants expressing SCN resistance and pesticides can be reduced by treating plant propagation material expressing SCN resistance with a nematode-antagonistic biocontrol agent. Examples of suitable combinations of SCN resistance source nematode-antagonistic biocontrol agent include, but are not limited to:

| SCN resistance source | Biocontrol agent |
|---|---|
| PI548402 | *Pasteuria* spp |
| PI548402 | *Bacillus* spp |
| PI437654 | *Pasteuria* spp |
| PI437654 | *Bacillus* spp |
| PI90763 | *Pasteuria* spp |
| PI90763 | *Bacillus* spp |
| PI209332 | *Pasteuria* spp |
| PI209332 | *Bacillus* spp |
| PI89882 | *Pasteuria* spp |
| PI89882 | *Bacillus* spp |
| PI548316 | *Pasteuria* spp |
| PI548316 | *Bacillus* spp |
| PI88788 | *Actinomycetes* spp. |
| PI88788 | *Agrobacterium* spp. |
| PI88788 | *Arthrobacter* spp. |
| PI88788 | *Alcaligenes* spp. |
| PI88788 | *Aureobacterium* spp. |
| PI88788 | *Azobacter* spp. |
| PI88788 | *Beijerinckia* spp. |
| PI88788 | *Burkholderia* spp. |
| PI88788 | *Chromobacterium* spp. |
| PI88788 | *Clavibacter* spp. |
| PI88788 | *Clostridium* spp. |
| PI88788 | *Comomonas* spp. |
| PI88788 | *Corynebacterium* spp. |
| PI88788 | *Curtobacterium* spp. |
| PI88788 | *Desulforibtio* spp. |
| PI88788 | *Enterobacter* spp. |
| PI88788 | *Flavobacterium* spp. |
| PI88788 | *Gluconobacter* spp. |
| PI88788 | *Hydrogenophage* spp. |
| PI88788 | *Klebsiella* spp. |
| PI88788 | *Methylobacterium* spp. |
| PI88788 | *Phyllobacterium* spp. |
| PI88788 | *Phingobacterium* spp. |
| PI88788 | *Photorhabdus* spp. |
| PI88788 | *Rhizobium* spp. |
| PI88788 | *Serratia* spp. |
| PI88788 | *Stenotrophomonas* spp. |

-continued

| SCN resistance source | Biocontrol agent |
|---|---|
| PI88788 | *Xenorhadbus* spp. |
| PI88788 | *Variovorax* spp. |
| PI88788 | *Pseudomonas* spp. |
| PI88788 | *Paenibacillus* spp |
| PI88788 | *Pasteuria* spp. |
| PI88788 | *Pasteuria penetrans* |
| PI88788 | *Pasteuria thornei* |
| PI88788 | *Pasteuria nishizawae* |
| PI88788 | *Pasteuria ramosa* |
| PI88788 | *Pasteuria usgae* |
| PI88788 | *Bacillus* spp |
| PI88788 | *Bacillus* sp B16 |
| PI88788 | *Bacillus agri* |
| PI88788 | *Bacillus aizawai* |
| PI88788 | *Bacillus albolactis* |
| PI88788 | *Bacillus amyloliquefaciens* |
| PI88788 | *Bacillus cereus* |
| PI88788 | *Bacillus coagulans* |
| PI88788 | *Bacillus endoparasiticus* |
| PI88788 | *Bacillus endorhythmos* |
| PI88788 | *Bacillus firmus* |
| PI88788 | *Bacillus kurstaki* |
| PI88788 | *Bacillus lacticola* |
| PI88788 | *Bacillus lactimorbus* |
| PI88788 | *Bacillus lactis* |
| PI88788 | *Bacillus laterosporus* |
| PI88788 | *Bacillus lentimorbus* |
| PI88788 | *Bacillus licheniformis* |
| PI88788 | *Bacillus megaterium* |
| PI88788 | *Bacillus medusa* |
| PI88788 | *Bacillus metiens* |
| PI88788 | *Bacillus natto* |
| PI88788 | *Bacillus nigrificans* |
| PI88788 | *Bacillus papillae* |
| PI88788 | *Bacillus pumilus* |
| PI88788 | *Bacillus siamensis* |
| PI88788 | *Bacillus sphaericus* |
| PI88788 | *Bacillus subtilis* |
| PI88788 | *Bacillus thuringiensis* |
| PI88788 | *Bacillus uniflagellate* |

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein, and every number between the end points. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10, as well as all ranges beginning and ending within the end points, e.g. 2 to 9, 3 to 8, 3 to 9, 4 to 7, and finally to each number 1, 2, 3, 4, 5, 6, 7, 8, 9 and 10 contained within the range. It is further noted that, as used in this specification, the singular forms "a," "an," and "the" include plural referents unless expressly and unequivocally limited.

The invention claimed is:

1. A method of reducing a rate at which soybean cyst nematode (SCN) pests acquire tolerances to pesticidal activity of soybean plants expressing SCN resistance and pesticides, the method comprising treating a seed expressing SCN resistance with a nematicide comprising at least one nematode-antagonistic biocontrol agent and planting said seed, wherein the nematode-antagonistic biocontrol agent is *Pasteuria* spp., and wherein the *Pasteuria* spp. is present in an amount from about $1\times10^5$ to about $1\times10^{12}$ spores of *Pasteuria* spp. per seed.

2. The method of claim 1, wherein said at least one nematode-antagonistic biocontrol agent is selected from the group consisting of *Pasteuria penetrans, Pasteuria thornei, Pasteuria nishizawae*, and *Pasteuria ramosa.*

3. The method of claim 1, further comprising treating said plant propagation material with an insecticide.

4. The method of claim 3, wherein said insecticide is selected from the group consisting of thiamethoxam, imidacloprid, clothianidin, thiacloprid, acetamiprid, beta-cyfluthrin, cyantraniliprole, diafenthiuron, diazinon, emamectin, emamectin benzoate, fenoxycarb, fipronil, flonicamid, lambda-cyhalothrin, methiocarb, pymetrozine, pyriproxyfen, pyrifluquinazon, spinetoram, spinosad, spirotetramat, tefluthrin, thiodicarb and Ti-435.

5. The method of claim 1, wherein said SCN resistance includes a resistance source selected from the group consisting of PI88788, PI548402, PI437654, PI90763, PI209332, PI89882 and PI548316.

6. The method of claim 5, wherein said SCN resistance includes resistance source PI88788.

7. A method of increasing yield of a plant propagation material expressing SCN resistance, the method comprising: treating a seed expressing SCN resistance with a nematicide comprising at least one nematode-antagonistic biocontrol agent, wherein the nematode-antagonistic biocontrol agent is *Pasteuria* spp., and wherein the *Pasteuria* spp. is present in an amount from about $1\times10^5$ to about $1\times10^{12}$ spores of *Pasteuria* spp. per seed.

8. The method of claim 7, wherein said at least one nematode-antagonistic biocontrol agent selected from the group consisting of *Pasteuria penetrans, Pasteuria thornei, Pasteuria nishizawae*, and *Pasteuria ramosa.*

9. The method of claim 7, wherein said SCN resistance includes a resistance source selected from the group consisting of PI88788, PI548402, PI437654, PI90763, PI209332, PI89882 and PI548316.

10. The method of claim 9, wherein the SCN resistance includes resistance source PI88788.

11. The method of claim 10, wherein the nematode-antagonistic biocontrol agent is *Pasteuria nishizawae.*

12. A method for increasing pesticidal activity on SCN pests, the method comprising treating a soybean seed expressing SCN resistance with a nematicide comprising at least one nematode-antagonistic biocontrol agent, wherein the nematode-antagonistic biocontrol agent is *Pasteuria* spp., and wherein the *Pasteuria* spp. is present in an amount from about $1\times10^5$ to about $1\times10^{12}$ spores of *Pasteuria* spp. per seed.

13. The method of claim 12, wherein said SCN resistance includes a resistance source selected from the group consisting of PI88788, PI548402, PI437654, PI90763, PI209332, PI89882 and PI548316.

14. The method of claim 13, wherein said SCN resistance includes resistance source PI88788.

15. A plant propagation material expressing SCN resistance, wherein the plant propagation material is a seed and wherein the plant propagation material is treated with a nematicide comprising at least one nematode-antagonistic biocontrol agent wherein the nematode-antagonistic biocontrol agent is *Pasteuria* spp., and wherein the *Pasteuria* spp. is present in an amount from about $1\times10^5$ to about $1\times10^{12}$ spores of *Pasteuria* spp. per seed.

16. The plant propagation material of claim 15, wherein said at least one nematode-antagonistic biocontrol agent is selected from the group consisting of *Pasteuria penetrans, Pasteuria thornei, Pasteuria nishizawae*, and *Pasteuria ramosa*.

17. The plant propagation material of claim 15, wherein said plant propagation material is further treated with an insecticide.

18. The plant propagation material of claim 17, wherein said insecticide is selected from the group consisting of thiamethoxam, imidacloprid, clothianidin, thiacloprid, acetamiprid, beta-cyfluthrin, cyantraniliprole, diafenthiuron, diazinon, emamectin, emamectin benzoate, fenoxycarb, fipronil, flonicamid, lambda-cyhalothrin, methiocarb, pymetrozine, pyriproxyfen, pyrifluquinazon, spinetoram, spinosad, spirotetramat, tefluthrin, thiodicarb and Ti-435.

19. The plant propagation material of claim 15, wherein said SCN resistance includes a resistance source selected from the group consisting of P188788, P1548402, P1437654, P190763, P1209332, P189882and P1548316.

20. The plant propagation material of claim 19, wherein said SCN resistance includes resistance source P188788.

* * * * *